June 30, 1959 D. H. MOREY, JR Plant Pat. 1,849
ROSE PLANT
Filed Nov. 12, 1958
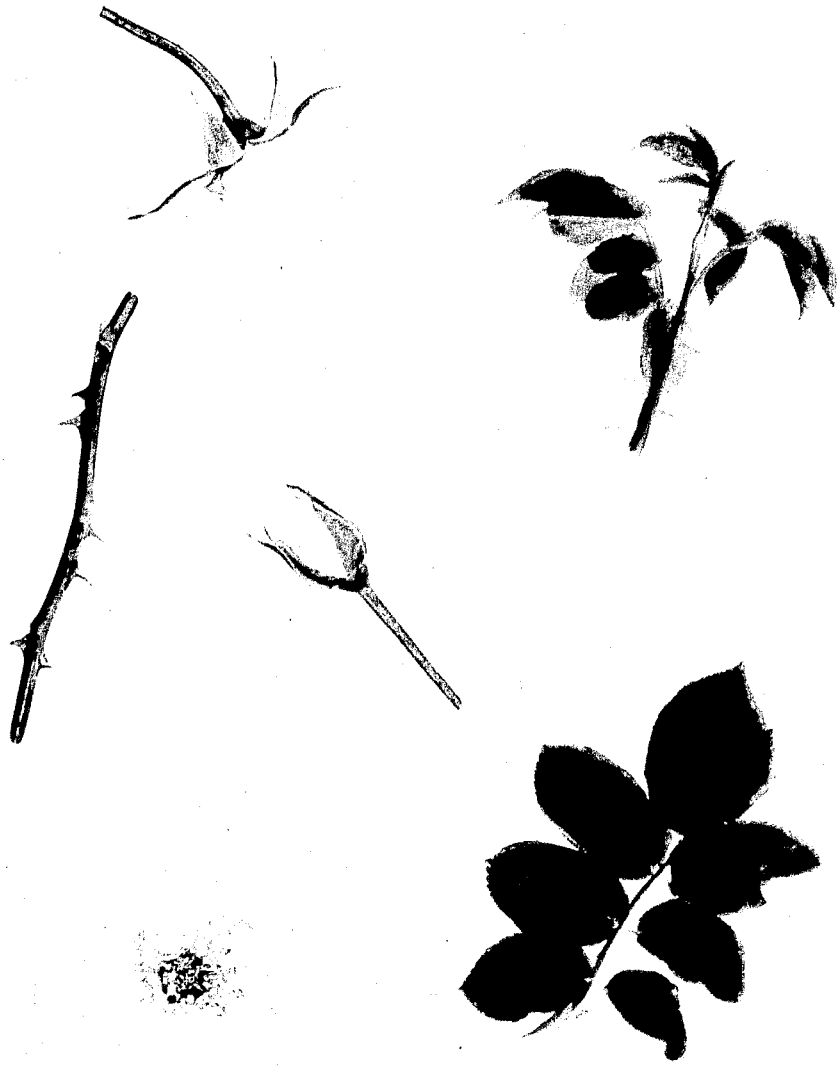
Inventor.
D. H. Morey, Jr.
By: Robert Robb
Attorneys.

United States Patent Office

Plant Pat. 1,849
Patented June 30, 1959

1,849

ROSE PLANT

Dennison H. Morey, Jr., Pleasanton, Calif., assignor to Jackson & Perkins Company, Newark, N.Y., a corporation of New York Application November 12, 1958, Serial No. 773,529

1 Claim. (Cl. 47—61)

The present invention relates to a new and distinct variety of rose plant of the climing hybrid tea class, which was originated by me by crossing an unnamed and unpatented large-flowered yellow climbing seedling with the hybrid tea variety "Lydia" (unpatented).

The primary objective of this breeding was to produce a climbing rose having large hybrid tea size flowers. This objective was fully achieved, along with other desirable features, as evidenced by the following unique combination of characteristics which are outstanding in the new variety, and which distinguish it from its parents, as well as from all other varieties of which I am aware:

(1) A climbing habit of plant growth;

(2) Excellent foliage which is retained to the base of the plant throughout the entire summer;

(3) Reblooming qualities which occur throughout the summer;

(4) Large flowers of the hybrid tea type; and (5) A distinctive Pinard Yellow color of the blooms, with the lower half of the petals lightly overcast with Empire Yellow, which is unusual in reblooming climbing hybrid tea roses.

Asexual reproduction of the new variety by budding, as performed at Newark, New York and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—An unnamed and unpatented large-flowered yellow climbing seedling.

*Pollen parent.*—"Lydia" (an unpatented hybrid tea).

Classification:

*Botanic.*—Climber.

*Commercial.*—Climber.

*Flower*

(Observations made from specimens grown outdoors at Newark, New York in the late morning in the latter part of August.)

Blooming habit: Recurrent—continuous.

Bud:

*Size.*—Medium.

*Form.*—Ovoid; is not affected by wet or hot weather.

*Color.*—When sepals first divide—Picric Yellow, Plate 4. When petals begin to unfurl—Lemon Chrome, Plate 4, with edges of petals lightly overcast with Coral Red, Plate 13. When half-blown: inside of petals—Pale Lemon Yellow, Plate 4, with outer edges of petals lightly overcast with Barium Yellow, Plate 16; reverse of petals—Empire Yellow, Plate 4, with outer edges of petals and center of petals lightly overcast with Citron Yellow, Plate 16.

*Sepals.*—Slightly branched; curl back when petals begin to unfurl. Color: inside—Pale Olivine, Plate 32; outside—Oil Green, Plate 5.

*Calyx.*—Color—Oil Green, Plate 5. Shape—funnel. Size—small. Aspect—smooth. Odor when rubbed—none.

*Peduncle.* — Length — medium. Aspect — smooth. Strength — erect; heavy. Color — Bice Green, Plate 17.

*Opening.*—Opens up well; is not affected by adverse weather conditions.

Bloom:

*Size.*—Medium. Average size when fully expanded —5 inches.

*Borne.*—Singly, and several together.

*Stems.*—Medium length; strong.

*Form (when first open).*—Cupped. Permanence—retains its form to the end.

*Petalage.*—Double (full but open center). Number of petals under normal conditions—45.

*Color.*—Center of flower—Light Cadmium, Plate 4. Outer petals—Martius Yellow, Plate 4, with center of petals lightly overcast with Empire Yellow, Plate 4. Base of petals (aiglet)—Empire Yellow, Plate 4. Inside of petals—Pinard Yellow, Plate 4, with lower half of petals lightly overcast with Empire Yellow, Plate 4. Reverse of petals—Sulphur Yellow, Plate 5. General tonality from a distance—Pinard Yellow, Plate 4, with lower half of petals lightly overcast with Empire Yellow, Plate 4.

*Discoloration.*—General tonality at end of first day—Light Cadmium, Plate 4, lightly overcast with Pinard Yellow, Plate 4. Second day—Pinard Yellow, Plate 4, lightly overcast with Empire Yellow, Plate 4. Third day—Pinard Yellow, Plate 4, lightly overcast with Empire Yellow, Plate 4.

Petals:

*Texture.*—Thick; is not affected by wet or hot weather.

*Appearance.*—Inside—satiny. Outside—shiny.

*Form.*—Oval; slightly notched.

*Arrangement.*—Imbricated (regularly arranged shingle-like).

*Petaloids in center.*—Few; small.

*Persistence.*—Drop off cleanly.

*Fragrance.* — Moderate. Nature — fruity (russet apple).

*Lasting quality.*—On the plant—long. As cut flower—long.

*Genital Organs*

Stamens, anthers: Medium size; many; regularly arranged around styles. Color—Light Orange-Yellow, Plate 3.

Stamens, filaments (threads): Long. Color—Carnelian Red, Plate 14.

Pollen: Color—Pale Orange-Yellow, Plate 3.

Styles: Bunched; uneven length; medium length; thin.

Stigmas: Color—Light Greenish Yellow, Plate 5.

Ovaries: All enclosed in calyx.

Hips: None.

Seeds: None.

*Plant*

Form: Climber.

Growth: Vigorous; upright.

Foliage: Compound of 5 to 7 leaflets.

*Size.*—Large.

*Quantity.*—Normal.

*Color.*—New foliage: upper side—Chromium Green, Plate 32, with edges of leaf and serrations Oxblood Red, Plate 1; under side—Oil Green, Plate 5, lightly overcast with Carmine, Plate 1. Old foliage: upper side—Dark Cress Green, Plate 31; under side—Light Cress Green, Plate 31.

*Shape.*—Oval pointed.

*Texture.*—Upper side—glossy. Under side—smooth.

*Ribs and veins.*—Ordinary.

*Edge.*—Serrated (saw-toothed).

*Serration.*—Both double and single; small.

*Leaf stem.*—Color—Spinach Green, Plate 5. Under side—prickly.

*Stipules.*—Medium length; smooth.

Wood:

*New wood.*—Color—Oil Green, Plate 5. Bark—smooth.

*Old wood.*—Color—Elm Green, Plate 17. Bark—smooth.

Thorns:

*Thorns.*—Quantity: on main stalks from base—many; on laterals from stalk—many. Form—narrow base; medium length; straight. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the climbing hybrid tea class, substantially as herein shown and described, characterized particularly as to novelty by the unique combination of a climbing habit of plant growth, excellent foliage which is retained to the base of the plant throughout the entire summer, reblooming qualities which occur throughout the summer, large flowers of the hybrid tea type, and a distinctive Pinard Yellow color of the blooms, with the lower half of the petals lightly overcast with Empire Yellow.

No references cited.